United States Patent [19]
Lee

[11] Patent Number: 5,737,429
[45] Date of Patent: Apr. 7, 1998

[54] PORTABLE VIEWABLE AND AUDIBLE STETHOSCOPE

[76] Inventor: Byung Hoon Lee, #7-402, Jinhung Apt., 65, Cheongdam-dong, Kangnam-Ku, Seoul 135-100, Rep. of Korea, 135-100

[21] Appl. No.: 616,482

[22] Filed: Mar. 19, 1996

[30] Foreign Application Priority Data

Mar. 28, 1995 [KR] Rep. of Korea ............... 1995/5784

[51] Int. Cl.$^6$ ................................................. A61B 7/04
[52] U.S. Cl. ................................. 381/67; 128/715
[58] Field of Search ........................ 381/67; 128/715; 181/131

[56] References Cited

U.S. PATENT DOCUMENTS

| | | |
|---|---|---|
| 4,594,731 | 6/1986 | Lewkowicz ............ 381/67 |
| 4,598,417 | 7/1986 | Deno ..................... 381/67 |
| 4,723,555 | 2/1988 | Shue ..................... 381/67 |
| 4,783,813 | 11/1988 | Kempka ................. 381/67 |
| 4,783,814 | 11/1988 | Foley .................... 381/67 |
| 4,792,145 | 12/1988 | Eisenberg et al. ...... 128/715 |
| 5,218,969 | 6/1993 | Bredesen et al. ....... 381/67 |
| 5,365,023 | 11/1994 | Lawton .................. 381/67 |

FOREIGN PATENT DOCUMENTS

| | | | |
|---|---|---|---|
| 4100607 | 7/1992 | Germany | .... 381/67 |
| 6450805 | 3/1989 | Japan . | |

*Primary Examiner*—Curtis Kuntz
*Assistant Examiner*—Ping W. Lee
*Attorney, Agent, or Firm*—Feix & Feix

[57] ABSTRACT

A portable viewable and audible stethoscope for visually and audibly monitoring the vital life signs (e.g. heart beat, lung respiration, artery pulse, intestinal sounds) of a patient. The stethoscope includes a large diameter sound absorbing cup and a small diameter sound absorbing connected to opposite ends of a tubular connector and an output device enclosed within a hand held case that is connected to a middle region of the tubular connector by a supporting tube. The tubular connector is provided with an internally installed microphone which converts the absorbed sounds to electrical signals. The output device includes an electronic circuit assembly for amplifying the signals from the microphone, an oscilloscope for displaying the signals, and a speaker for converting the signals into audible sounds. The outside of the case of the output device is provided with control switches for the oscilloscope display, speaker volume adjustment and power on/off. The case further includes a small replaceable battery to supply power to the electronic circuits. The stethoscope is simple in its structure, and can be conveniently carried. The stethoscope can be used by both professional and ordinary people and it allows the condition of a patient to be monitored visually and audibly by many surrounding people.

15 Claims, 4 Drawing Sheets

PORTABLE VIEWABLE AND AUDIBLE STETHOSCOPE

FIELD OF THE INVENTION

The present invention relates to a diagnosing stethoscope. Particularly the present invention relates to a portable viewable and audible stethoscope which does not have receivers and sound tubes for transmitting sounds to human ears. However, the stethoscope includes: a pair of sound absorption cups for absorbing sounds; a microphone for converting the absorbed sounds to electrical signals; an electronic circuit assembly for amplifying the electrical signals; a speaker for outputting sounds; a picture screen for displaying the curves of sounds. The above components are accommodated within a small case, so that it can be conveniently carried. Further, this stethoscope can be used not only by professional people but also by the ordinary people. Further, the stethoscope gives not only audible sounds but also viewable pictures.

DESCRIPTION OF THE PRIOR ART

Generally, a stethoscope is an audible diagnosing device for monitoring the pulsation sounds of heart, respiration sounds of lungs, sounds of artery, and sounds of intestines, whereby the healthiness or sickliness of a person can be diagnosed.

The general stethoscope includes a sound absorbing cup, two rubber tubes for transmitting the absorbed sounds, and two receivers connected to the ends of the rubber tubes so as to be put into ears, the stethoscope being Y shaped. Thus the diagnosing person can sense the sounds of the stethoscope. However, in such a conventional stethoscope, only the diagnosing person (doctor) can hear the sounds, but other persons including the patient, the protector for the patient, and nurses cannot hear the sounds.

However, there are stethoscopes in which all the nearby persons can hear the sounds, or the sounds are displayed in graphs.

One of them is disclosed in Japanese Utility Model Laid-open No. Sho-64-50805. This is an electronic stethoscope, and includes: an electronic recorder for recording the sounds in the form of graphs; a microphone for sensing the sounds; and earphones for being put into ears. However, in this stethoscope, only the doctor can hear the sounds, and the recording device is installed in the diagnosing room. That is, the recording device is not a portable type.

Meanwhile, U.S. Pat. No. 5,003,605 discloses an electronic stethoscope giving timing sounds. The principle feature of this stethoscope is to provide an electronic circuit for amplifying the amplitude of the absorbed sounds. In this stethoscope, however, visible graphs are not provided.

U.S. Pat. No. 4,783,813 discloses an electronic stethoscope provided with a blood flow indicator. This stethoscope visibly indicates the sounds of blood flow and the respiratory sounds, but is for professional use.

U.S. Pat. No. 4,598,417 also discloses an electronic stethoscope. In this stethoscope, the principle feature is that the absorbed sounds are amplified to make it possible to hear the sounds through ear phones. This stethoscope is also for professional use.

As described above, in the conventional stethoscopes, the absorbed sounds cannot be sensed visually, and it is difficult to use them by people other than professional people, as well as being non-portable. Thus most of them are for professional use.

Therefore, the conventional stethoscopes cannot be used in homes by ordinary people. Further, they cannot be used by rescue teams. Therefore, rescue teams also are using the primitive type stethoscope consisting of a sound absorbing cup, two rubber tubes and two receivers.

However, in the case where a patient has lost consciousness at home, or an accident has occurred to a person, there is a need to quickly confirm in a simple manner whether or not the person is still breathing. Therefore, there is a demand for a stethoscope which is lightweight and portable such that it easily carried in a simple manner, and which includes audible means which enable surrounding people to hear the absorbed sounds, and which also includes graphical display means for displaying the person's vital sign on a viewable screen display in a readily understandable manner. These need to be done not only by professional people but also by ordinary people.

SUMMARY OF THE INVENTION

The present invention is intended to overcome the above described problems of the conventional techniques.

Therefore it is an object of the present invention to provide a portable viewable and audible stethoscope in which a family can use it conveniently, and a rescue team may be equipped with it.

It is another object of the present invention to provide a portable viewable and audible stethoscope in which a sound absorbing cup with a large diameter and another sound absorbing cup with a small diameter are connected to the opposite ends of a tubular connector, and a supporting tube is connected between the middle of the tubular connector and a case of an output device.

The stethoscope of the present invention does not have receivers or sound tubes for transmitting the absorbed sounds.

In the middle of the tubular connector, there is internally installed a microphone, and the microphone converts the absorbed sounds to electrical signals. The case of the output device accommodates an electronic circuit assembly for amplifying the signals from the microphone. On the top of the case, there is disposed an oscilloscope. At a side of the oscilloscope, there is installed a speaker, while, on another side of the oscilloscope, there are disposed a power source and sound volume adjusting switch and a switch for the oscilloscope. Further, a small battery is installed within the case, so as to supply the power to the electronic circuits.

The principle feature of the present invention is that the case of the output device accommodating the electronic circuit assembly, the oscilloscope and the speaker is integrally coupled with a pair of the sound absorbing cups in a simple manner.

Therefore it is convenient to carry, and there is no bulky receiver. However, the absorbed sounds are amplified into large sounds, so that all the surrounding people can hear the sounds. Further, if a patient or a person hurt in an accident is diagnosed with this stethoscope, not only professional personnel but also ordinary person can know whether the patient is slightly breathing or not, whether the heart pulsates, or whether the patient has died, by monitoring the sounds of the speaker and the graphs of the oscilloscope.

Therefore, this stethoscope may be kept in the home to diagnose the family in an emergency case, and particularly, a rescue team may be equipped with this stethoscope to use it in an accident.

BRIEF DESCRIPTION OF THE DRAWINGS

The above object and other advantages of the present invention will become more apparent by describing in detail the preferred embodiment of the present invention with reference to the attached drawings in which.

DESCRIPTION OF THE PREFERRED EMBODIMENT

Figure 1:
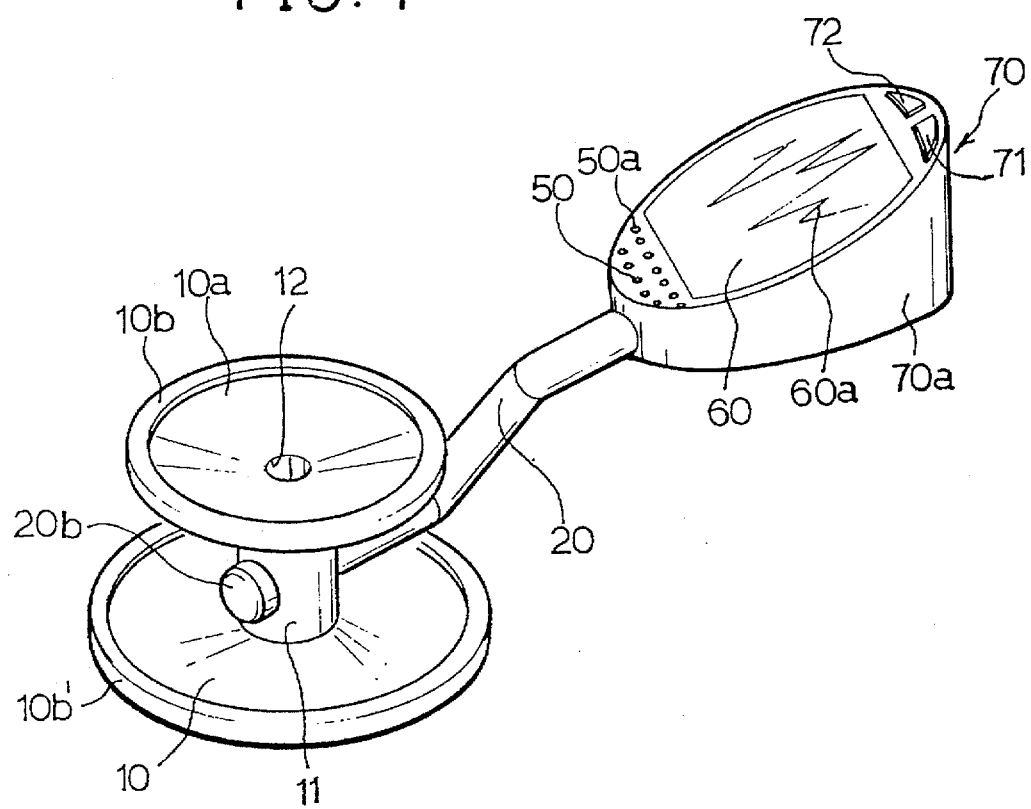
FIG. 1 is an exemplary perspective view of the stethoscope according to the present invention.
Figure 2:
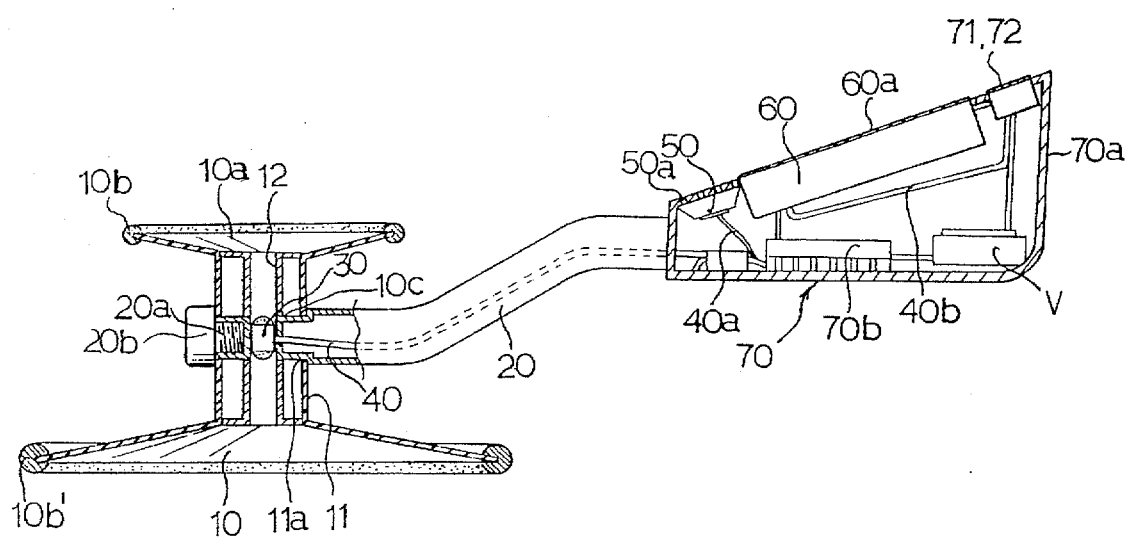
FIG. 2 is a sectional view showing the constitution of the stethoscope according to the present invention.
Figure 3:
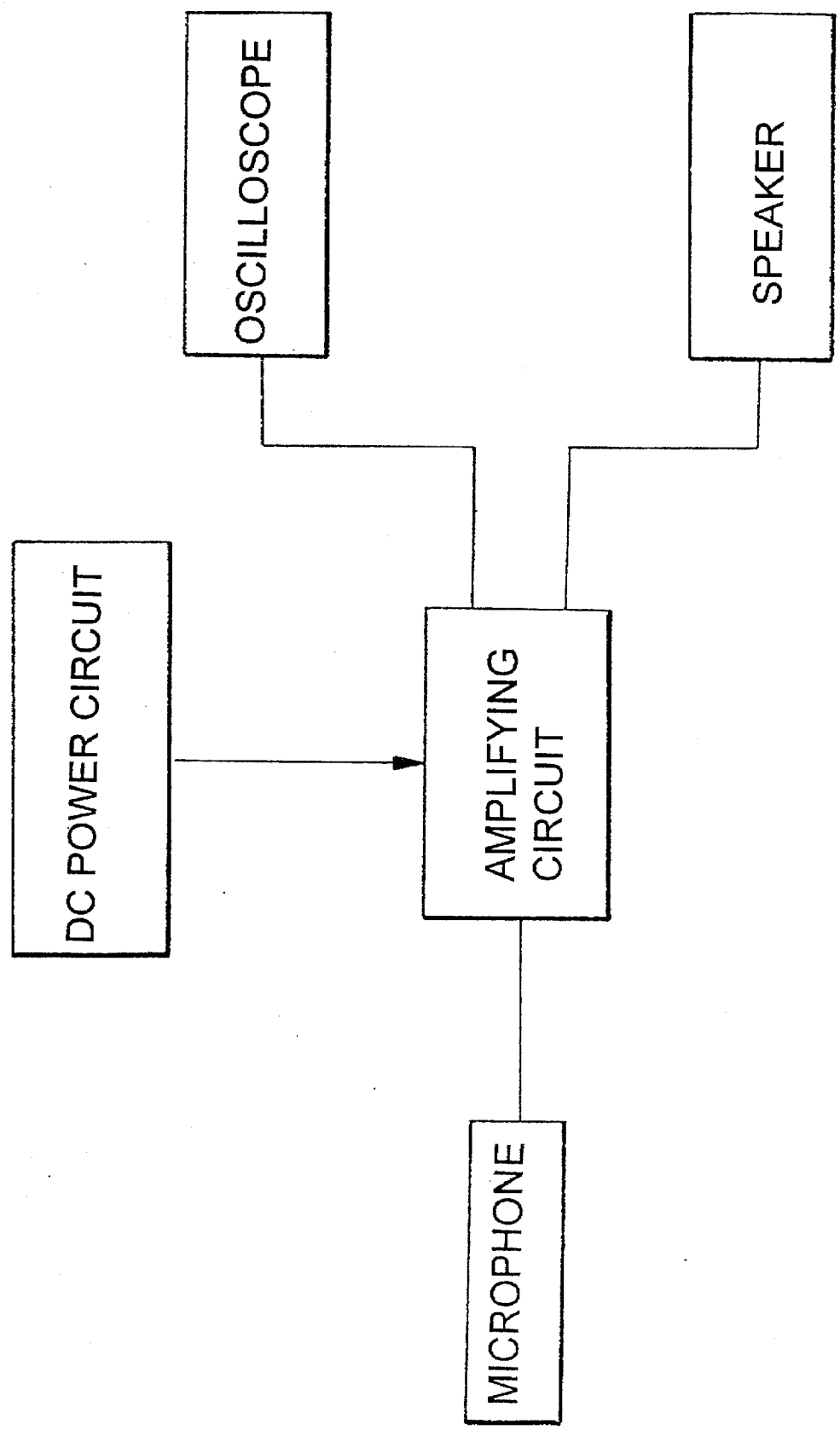
FIG. 3 is a block diagram showing the constitution of the electronic circuit according to the present invention.
Figure 4:
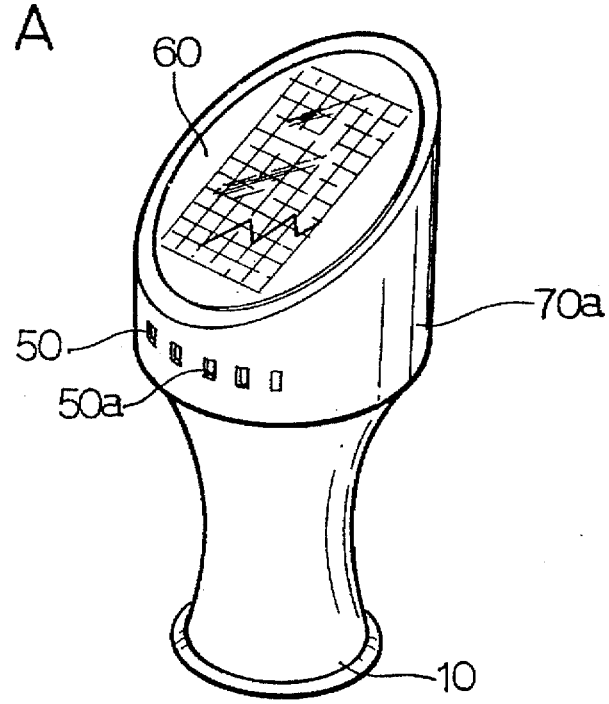
FIGS. 4A and 4B illustrates other embodiments of the stethoscope according to the present invention.
Figure 4:
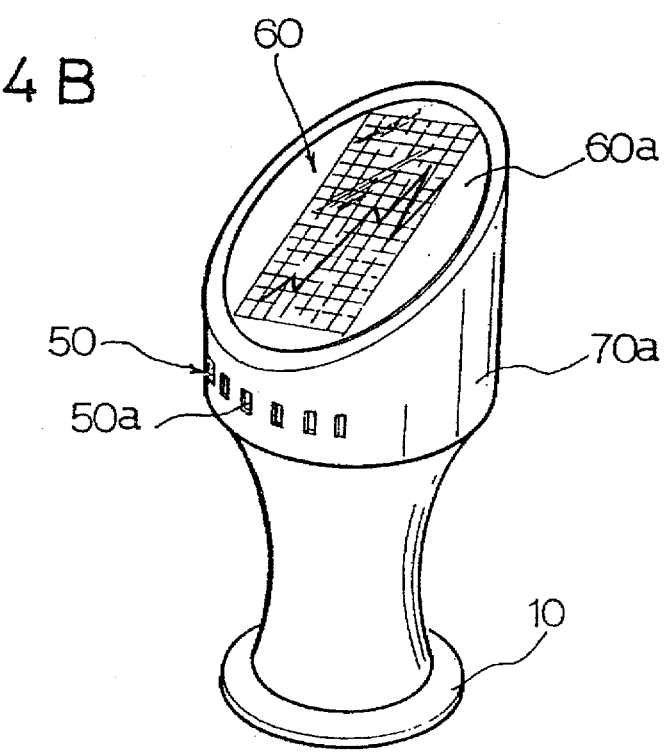

The portable visible and audible stethoscope according to the present invention is constituted as shown in FIGS. 1 and 2.

On the opposite ends of a tubular connector 11, there are connected a sound absorbing cup 10 with a large diameter and a sound absorbing cup 10a with a smaller diameter, and each of the sound absorbing cups 10 and 10a has a sound inlet. Further, annular ribs 10b and 10b' are formed on the circumferences of the sound absorbing cups 10 and 10a, to enable the sound absorbing cups to closely contact a human body. Further, the small sound absorbing cup 10a is for diagnosing children, and the large sound absorbing cup 10 is for diagnosing adults.

Further, a supporting tube 20 extends from a side of an elliptical case 70a of an output device 70, and the supporting tube 20 is bent at two points. One end of the supporting tube 20 is inserted into a hole 10c which is formed at the middle of the tubular connector 11, whereby the tubular connector 11 and the supporting tube 20 are coupled together in a T shape.

The hole 10c is a through hole, and the tip portion of the supporting tube has female threads 20a into which a screw 20b is threadably inserted, whereby the case 70a is coupled with the two sound absorbing cups 10 and 10a so as to form an integral structure. The case 70a serves as a handle for the stethoscope when it is being used.

The tubular connector internally accommodates a microphone 30 which converts the sounds coming from the two sound absorbing cups 10 and 10a through sound inlets 12 into electrical signals.

On the middle portion of the top of the case 70a of the output device 70, there is installed an oscilloscope 60 in an inclined form, so that graphs can be watched through a picture screen 60a.

On the lower side on the top of the case 70a adjacently to the oscilloscope 60, there are formed a plurality of holes 50a of a speaker 50, while on the higher side, there are installed an oscilloscope switch 71 and a speaker switch 72 side by side. These switches 71 and 72 have the function of turning on and off the power source, and the function of adjusting the sound volume.

Further, the case internally accommodates an electronic circuit assembly 70b which includes an amplifying circuit for amplifying the electrical signals from the microphone, and an electronic circuit for displaying the electrical signals into graphs. This electronic circuit assembly is not the principle feature of the present invention, because it is composed of the known circuits.

An electrical wire 40 of the microphone 30 is connected through the interior of the supporting tube 20 to an input terminal of the electronic circuit assembly 70b, in such a manner that the electronic circuit assembly 70b should electronically operate.

Meanwhile, a speaker wire 40a and an oscilloscope wire 40b are connected to the output side of the electronic circuit assembly 70b. Further, a small battery v is installed within the case. This battery is preferably a replaceable or rechargeable one, and supplies power to the electronic circuit assembly 70a.

The stethoscope of the present invention does not include receivers and the sound transmitting tubes.

The stethoscope of the present invention constituted as above will now be described as to its operation and effect.

The stethoscope of the present invention is used by families for diagnosing family members in the home and by rescue teams for diagnosing those hurt in accidents.

In using the stethoscope of the present invention, first the switches 71 and 72 are turned on. If the switches 71 and 72 are turned on, the power is supplied from the battery v to the electronic circuit assembly 70b, thereby energizing the electronic circuit assembly 70b.

Then holding the case 70a as the handle, the rib 10b or 10b' of the sound absorbing cup 10 or 10a is made to closely contact to the body of the patient, and then, the produced sounds are listened. If the sound absorbing cup 10 or 10a is contacted to the chest, the respiratory sound can be heard. If it is contacted to below the chest, the pulsating sounds of heart can be heard. If it is contacted to the belly, the sounds of intestine can be heard. The sounds from the human body are guided into the sound inlet 12 by the sound absorbing cup 10 or 10a, and these sounds are converted into electrical signals by the microphone 30.

The electrical signals are amplified by the electronic circuit assembly 70b of the output device 70, and the amplified signals are supplied from the output section of the electronic circuit assembly 70b through the leading wire 40a to the speaker 50, with the result that the diagnosing loud sounds are produced. These sounds can be heard to all the surrounding persons.

Meanwhile, the amplified electrical signals are also supplied from the output section of the electronic circuit assembly 70b through the leading wire 40b to the oscilloscope 60, with the result that graphs appear on the picture screen.

A professional person will know the state of the illness based on the produced sounds and the graphs. However, in fact, in general families and rescue teams, it will be known only so to whether the heart beat is weak, or the respiration has been stopped. Probably this will be sufficient. If the respiration and heart beat are stopped, the speaker will produce no respiration sounds, and no pulsation sounds. Further the picture screen will show only a straight line, and therefore, even a non-professional person will know about the death of the patient. Therefore, the death time can be accurately recorded, and the record will become an important data for handling the accident.

As the diagnosed results are known to all the surrounding people, the people can cooperatively handle the matter. In the case of an emergency, an ambulance can be quickly called to send the patient to a hospital.

The conventional stethoscopes are not for these purposes, but the stethoscope of the present invention can be used in judging on the state of a patient in an emergency case. Further, it is simple in its structure, and can be conveniently carried.

The battery may be a replaceable battery or a rechargeable battery, so that it can be replaced or recharged upon exhaustion. Further, there are no lengthy sound transmitting tubes, and therefore, it is convenient to carry. Therefore, anyone may use the stethoscope of the present invention in the above described cases.

What is claimed is:

1. A portable viewable and audible stethoscope comprising:
   a pair of sound absorption cups, each of said sound absorption cups provided with an annular rim to permit comfortable, close contact with a patient's body for absorbing sounds produced within the patient's body;
   said pair of sound absorption cups further including:
      a first sound absorption cup having a cup diameter sized sufficiently large for absorbing, sounds from a chest area of an adult;
      a second sound absorption cup having a cup diameter sized smaller than said cup diameter of said first sound absorption cup for absorbing sounds from a chest region of a child;
   a tubular connector for connecting said pair of sound absorption cups to opposite ends thereof such that said pair of sound absorption cups are disposed in back to back relationship to each other;
   a microphone for converting the absorbed sounds to electrical signals;
   an electronic circuit assembly for amplifying the electrical signals;
   a speaker for outputting sounds;
   a picture screen for displaying the curves of the absorbed sounds in graphs;
   a hand held case for accommodating said electronic circuit assembly, said speaker and said picture screen; and
   a rigid supporting tube including a first end portion, a middle portion and a second end portion, wherein:
      said first end portion is integrally coupled to said case;
      said second end portion is freely rotatably coupled to said tubular connector; and whereby rotation of said tubular connector about said supporting tube permits a desired one of said first and second sound absorption cups to be oriented in a downward position for close contact with the chest region of the patient's body while said case and picture screen are oriented in a desired upward, viewable position.

2. The portable viewable and audible stethoscope as claimed in claim 1, wherein said microphone is installed within said tubular connector, for converting the sounds absorbed by said sound absorbing cups into said electrical signals.

3. The portable viewable and audible stethoscope as claimed in claim 2, further comprising microphone lead wires connected to an input side of said electronic circuit assembly.

4. The portable viewable and audible stethoscope as claimed in claim 1, further comprising an oscilloscope installed on a central portion of the top of said case, for displaying the sounds in graphic curves.

5. The portable viewable and audible stethoscope as claimed in claim 4, wherein said speaker is installed at a side of said oscilloscope.

6. The portable viewable and audible stethoscope as claimed in claim 5, further comprising a speaker switch and an oscilloscope switch installed at another side of said oscilloscope.

7. The portable viewable and audible stethoscope as claimed in claim 5, further comprising speaker lead wires and oscilloscope lead wires connected to an output side of said electronic circuit assembly.

8. The portable viewable and audible stethoscope as claimed in claim 4, further comprising speaker lead wires and oscilloscope lead wires connected to an output side of said electronic circuit assembly.

9. The portable viewable and audible stethoscope as claimed in claim 4, wherein a picture screen of said oscilloscope is inclinedly installed.

10. The portable viewable and audible stethoscope as claimed in claim 1, further comprising microphone lead wires connected to an input side of said electronic circuit assembly.

11. The portable viewable and audible stethoscope as claimed in claim 1, further comprising a power supplying battery installed within said case.

12. The portable viewable and audible stethoscope as claimed in claim 1, wherein said middle portion of said supporting tube between said case and said tubular connector is oppositely bent at two points to provide a desired height offset between said pair of sound absorption cups and said case, said offset for facilitating diagnosis whereby said hand held case may be held in a substantially horizontal position above the patient's chest.

13. The portable viewable and audible stethoscope as claimed in claim 1, further comprising a screw threadably coupled to a terminal end of said second end portion of said supporting tube, said screw including an oversized cap portion for preventing uncoupling of said tubular connector from said supporting tube second end portion.

14. The portable viewable and audible stethoscope as claimed in claim 1, further comprising speaker lead wires and oscilloscope lead wires connected to an output side of said electronic circuit assembly.

15. The portable viewable and audible stethoscope as claimed in claim 1, further comprising a power supplying battery installed within said case.

* * * * *